United States Patent
Kidd et al.

(10) Patent No.: US 12,230,384 B2
(45) Date of Patent: Feb. 18, 2025

(54) MEDICAL TOOL AIDING DIAGNOSED PSYCHOSIS PATIENTS IN DETECTING AUDITORY PSYCHOSIS SYMPTOMS ASSOCIATED WITH PSYCHOSIS

(71) Applicants: Centre for Addiction and Mental Health, Toronto (CA); Memotext Corporation, Toronto (CA)

(72) Inventors: Sean Andrew Kidd, Toronto (CA); Amos Adler, Toronto (CA); Hesamaldin Nekouei, Richmond Hill (CA); Linda Kaleis, Newmarket (CA)

(73) Assignees: Centre for Addiction and Mental Health, Toronto (CA); Memotext Corporation, Toronto (CA)

( * ) Notice: Subject to any disclaimer, the term of this patent is extended or adjusted under 35 U.S.C. 154(b) by 0 days.

(21) Appl. No.: 18/363,529

(22) Filed: Aug. 1, 2023

(65) Prior Publication Data

US 2023/0377718 A1 Nov. 23, 2023

Related U.S. Application Data

(63) Continuation of application No. 17/819,603, filed on Aug. 12, 2022, now Pat. No. 11,763,929, which is a
(Continued)

(51) Int. Cl.
*G16H 20/70* (2018.01)
*A61B 5/00* (2006.01)
(Continued)

(52) U.S. Cl.
CPC ........... *G16H 20/70* (2018.01); *A61B 5/0022* (2013.01); *A61B 5/165* (2013.01); *A61B 5/746* (2013.01);
(Continued)

(58) Field of Classification Search
CPC ...... G16H 20/70; A61B 5/0022; A61B 5/165; A61B 5/746; A61B 5/4803; A61M 21/00
See application file for complete search history.

(56) References Cited

U.S. PATENT DOCUMENTS

| 4,975,960 A | 12/1990 | Petajan |
| 5,371,551 A | 12/1994 | Logan et al. |
(Continued)

FOREIGN PATENT DOCUMENTS

| CN | 104067341 B | 3/2017 |
| CN | 104246877 B | 5/2017 |
(Continued)

OTHER PUBLICATIONS

Anonymous, Schizophrenia: Helping Someone Who Is Hallucinating, Nov. 8, 2019, Retrieved on Jan. 17, 2024 from the Internet: URL:https://web.archive.org/web/20191108032248/https://myhealth.alberta.ca/Health/pages/conditions.aspx?hwid=aa48238.
(Continued)

*Primary Examiner* — Jay Trent Liddle
*Assistant Examiner* — Alyssa N Brandley
(74) *Attorney, Agent, or Firm* — Knobbe, Martens, Olson & Bear, LLP

(57) ABSTRACT

A medical tool is described for supporting an individual suffering from a mental condition or disorder characterized by auditory psychosis symptoms. The tool can assist in training the individual to distinguish between an acute auditory psychosis episode and ambient sounds. The tool can monitor for a non-audio input by a patient, where the input represents an indication that the patient is hearing sounds potentially symptomatic of psychosis. A microphone can monitor ambient sounds, which are tested against a threshold to determine and whether an auditory psychosis episode may be occurring.

25 Claims, 12 Drawing Sheets

Related U.S. Application Data continuation of application No. 16/777,633, filed on Jan. 30, 2020, now abandoned, which is a continuation-in-part of application No. 16/109,394, filed on Aug. 22, 2018, now abandoned.

(51) Int. Cl.
*A61B 5/16* (2006.01)
*A61M 21/00* (2006.01)

(52) U.S. Cl.
CPC ........... *A61M 21/00* (2013.01); *A61B 5/4803* (2013.01); *A61B 2562/0204* (2013.01); *A61M 2021/0027* (2013.01); *A61M 2205/18* (2013.01); *A61M 2205/3375* (2013.01); *A61M 2205/50* (2013.01)

(56) References Cited

U.S. PATENT DOCUMENTS

| | | | |
|---|---|---|---|
| 9,230,539 | B2 | 1/2016 | Pakhomov |
| 9,240,188 | B2 | 1/2016 | Paul et al. |
| 9,369,814 | B2 | 6/2016 | Victorian et al. |
| 9,721,565 | B2 | 8/2017 | Perlmutter |
| 9,747,894 | B2 | 8/2017 | Hsu et al. |
| 9,772,817 | B2 | 9/2017 | Jarvis et al. |
| 10,171,922 | B2 | 1/2019 | Merks |
| 2008/0246629 | A1 | 10/2008 | Tsui et al. |
| 2009/0043581 | A1 | 2/2009 | Abbott et al. |
| 2009/0112114 | A1 | 4/2009 | Ayyagari et al. |
| 2011/0313315 | A1 | 12/2011 | Attias et al. |
| 2012/0029383 | A1 | 2/2012 | Henriksen et al. |
| 2012/0329420 | A1 | 12/2012 | Zotti et al. |
| 2013/0065569 | A1 | 3/2013 | Leipzig et al. |
| 2014/0172310 | A1 | 6/2014 | Chin et al. |
| 2015/0288797 | A1 | 10/2015 | Vincent |
| 2015/0313529 | A1 | 11/2015 | Nevo et al. |
| 2015/0370994 | A1 | 12/2015 | Madan et al. |
| 2016/0140986 | A1 | 5/2016 | Bowers et al. |
| 2016/0203832 | A1 | 7/2016 | Paul et al. |
| 2016/0317781 | A1 | 11/2016 | Proud |
| 2017/0193982 | A1 | 7/2017 | Agrawal et al. |
| 2017/0323485 | A1 | 11/2017 | Samec et al. |
| 2017/0365101 | A1 | 12/2017 | Samec et al. |
| 2018/0322950 | A1 | 11/2018 | Cronin et al. |
| 2018/0366144 | A1* | 12/2018 | Ashoori ................. G16H 40/63 |
| 2019/0385711 | A1 | 12/2019 | Shiiriberg et al. |
| 2020/0066406 | A1 | 2/2020 | Kidd et al. |
| 2020/0077902 | A1 | 3/2020 | Angle et al. |
| 2020/0168317 | A1 | 5/2020 | Kidd et al. |
| 2022/0165253 | A1 | 5/2022 | Sharifi et al. |
| 2023/0052926 | A1 | 2/2023 | Kidd et al. |

FOREIGN PATENT DOCUMENTS

| | | |
|---|---|---|
| CN | 107111672 A | 8/2017 |
| DK | 2882204 T3 | 1/2017 |
| EP | 1545302 A4 | 12/2008 |
| KR | 101639933 B1 | 7/2016 |
| TW | I474317 B | 2/2015 |
| WO | WO 2002/014547 A2 | 10/2003 |
| WO | WO 2004/030532 A1 | 4/2004 |
| WO | WO 2008/091947 A3 | 11/2008 |
| WO | WO 2009/082743 A2 | 7/2009 |

OTHER PUBLICATIONS

Extended European Search Report mailed Jan. 26, 2024 for EP Application No. 20916321 in 5 pages.
Office Action mailed Oct. 19, 2023 for CA Application No. 3168925 in 4 pages.
Thomas, et al., Potential Applications of Digital Technology in Assessment, Treatment, and Self-help for Hallucinations, Schizophrenia Bulletin, vol. 45, Suppl. No. 1 pp. S32-S42, Feb. 1, 2019.
Office Action for CA Application No. 3,015,178 dated Feb. 28, 2023, in 5 pages.
Dodgson et al., Avoiding False Negatives: Are Some Auditory Hallucinations An Evolved Design Flaw?, Behavioural and Cognitive Psychotherapy, 37(3), pp. 325-334, 2009.
Ford, J.M. et al., "Neurophysiological studies of auditory verbal hallucinations", Schizophr Bull. vol. 38, Issue 4, pp. 715-723, Feb. 23, 2012.
HealthLink BC, Schizophrenia: Helping Someone Who Is Hallucinating, https;//www.healthlinkbc.ca/health-topics/aa48238, Sep. 11, 2018.
Ito, A. et al., Detection of Abnormal Sound Using Multi-stage GMM for Surveillance Microphone, 2009 Fifth International Conference on Information Assurance and Security, Xi'an, 2009, pp. 733-736, Aug. 20, 2009.
International Search Report and Written Opinion for Application No. PCT/CA2020/050218 dated Sep. 21, 2020 in 9 pages.
Cordova-plugin-media computer code retrieved from https://www.npmjs.com/package/cordova-plugin-media.
Cordova-plugin-media computer code retrieved from https:/cordova.apache.org/docs/en/latest/reference/cordova-plugin-media/.
European Telecommunications Standards Institute, Digital cellular telecommunications system; Voice Activity Detection (VAD) for Enhanced Full Rate (EFR) speech traffic channels, 1996, European Telecommunications Standards Institute.
Faizan Shaikh, Getting Started with Audio Data Analysis using Deep Learning, 2017, Vidhya Analytics <www.analyticsvidhya.com/blog/>.
Google Patent Search—"voice detection" from Apr. 20, 2020.
Google Search "Voice detection schizophrenia" from Apr. 20, 2020.
J. Kim, Voice Activity Detection Toolkit, Apr. 20, 2020, GitHub <https://github.com/jtkim-kaist/VAD>.
Jongseo Sohn et al., A statistical Model-Based Voice Activity Detection, 1999, GitHub <github.com/eesungkim/Voice_Activity_Detector>.
Listener computer code retrieved from https://github.com/shriphanl/Listener.
Math Works, G. 729 Voice Activity Detection, Apr. 20, 2020, Math Works <www.mathworks.com/>[help/dsp/examples/g-729-voice-activity-detection.html].
M.H. Moattar & M.M. Homayounpour, A Simple but Efficient Real-Time Voice Activity Detection Algorithm, Aug. 24-28, 2009, 17th European Signal Processing Conference (EUSIPCO 2009).
Python interface to the Google WebRTC Voice Activity Detector (VAD) computer code retrieved from https://pypi.org/project/webrtcvad/.
Recording and Saving Audio in Cordova Applications computer code retrieved from https://dzone.com/articles/recording-and-saving-audio-in-cordova-applications.
Schwoebel, Jim, An Introduction to Voice Computing in Python, Boston: NeuroLex Labratories, 2018, GitHub <github.com/jim-schwoebel/voicebook>.
Sehgal et al., A Convolutional Neural Network Smartphone App for Real-Time Voice Activity Detection, IEEE Access, vol. 6, Mar. 13, 2018, pp. 9017-9026, Department of Electrical and Computer Engineering, University of Texas at Dallas, Richardson TX.
Speech Recognition computer code retrieved from https://github.com/Uberl/speech_recognition/blob/master/LICENSE-FLAC.txt.
Speech Recognition computer code retrieved from https://github.com/Uberl/speech_recognition/blob/master/speech_recognition/_init_.py.
Wahib-Ul-Haq, Android Speaker Audio Analysis, Apr. 20, 2020, GitHub <github.com>[/wahibhaq/android-speaker-audioanalysis/tree/master/Android].
Cordova-Plugin-Media, Retrieved from the Internet on Nov. 21, 2018, URL: https://www.npmjs.com/package/cordova-plugin-media.
DZone, Recording and Saving Audio in Cordova Applications, Retrieved from the Internet on Nov. 21, 2018, URL:https://dzone.com/articles/recording-and-saving-audio-in-cordova-applications.
How Music Works, Sound and Music, Retrieved from the Internet on Nov. 21, 2018, URL: http://www.howmusicworks.org/103/Sound-and-Music/Amplitude-and-Frequency.

(56) References Cited

OTHER PUBLICATIONS

Analytics Vidhya, Getting Started with Audio Data Analysis using Deep Learning (with case study), Retrieved from the Internet on Nov. 21, 2018, URL: https://www.analyticsvidhya.com/blog/2017/08/audio-voice-processing-deep-learning/.

* cited by examiner

```
$scope.my_media    =    new   Media(  AudioSrc,  function(  status
){console.log(status);}, function( fail ){console.log(fail);});

$scope.recordMic = function(data){
        //console.log(data);
            if(data.isOn){

// Record audio
        $scope.my_media.startRecord();
        promise = $interval(function(){
            // get media amplitude
            $scope.my_media.getCurrentAmplitude(
                // success callback
                function (amp) {
                    console.log(amp + "%");
                    if( amp > 0.060 ){

$scope.SoundDetected = true;
                        unit = (amp * 200);
                    }else{
                            unit = 1;
                            $scope.SoundDetected = false;
                    }
                },
                // error callback
                function (e) {
                    console.log("Error getting amp=" + e);
                }
            );
        }, 400);
        /*
        $timeout(function() {
          $interval.cancel(promise);
        }, 60000);
        */
            }else{
                $interval.cancel(promise);
                $scope.my_media.stopRecord();
                if (devicePlatform == "Android"){
                    $scope.my_media.release();
                }
                $scope.SoundDetected = false;
                $timeout(function() {
                    unit = 0;
                    draw();
                }, 500);
            }

```
draw.seconds = 0;
draw.t = 0;

/**
 * Function to draw sine
 *
 * The sine curve is drawn in 10px segments starting at the
origin.
 */
function drawSine(t) {

// Set the initial x and y, starting at 0,0 and
translating to the origin on
    // the canvas.
    var x = t;
    var y = Math.sin(x);
    context.moveTo(yAxis, unit*y+xAxis);

// Loop to draw segments
    for (i = yAxis; i <= width; i += 10) {
        x = t+(-yAxis+i)/unit;
        y = Math.sin(x);
        context.lineTo(i, unit*y+xAxis);
    }
}
    Humble.Trig.init();

$scope.$on("$destroy", function(){
            $interval.cancel(promise);
            $scope.my_media.stopRecord();
            if (devicePlatform == "Android"){
                $scope.my_media.release();
            }
        });

```
draw = function () {

// Clear the canvas
    context.clearRect(0, 0, width, height);

// Set styles for animated graphics
    context.save();
    context.strokeStyle = '#8A2BE2';
    context.fillStyle = '#fff';
    context.lineWidth = 4;

// Draw the sine curve at time draw.t, as well as the
circle.
    context.beginPath();
    drawSine(draw.t);
    context.stroke();

// Restore original styles
    context.restore();

// Update the time and draw again
    draw.seconds = draw.seconds - .001;
    draw.t = draw.seconds*Math.PI;
    setTimeout(draw, 1);
};
```

500

FIG. 5

MEDICAL TOOL AIDING DIAGNOSED PSYCHOSIS PATIENTS IN DETECTING AUDITORY PSYCHOSIS SYMPTOMS ASSOCIATED WITH PSYCHOSIS

TECHNICAL FIELD

The present technology relates to a medical tool for assisting individuals experiencing acute instances of a key symptom of psychotic illness, namely auditory hallucinations, to differentiate between hallucinations and ambient sounds in the environment.

BACKGROUND

Psychosis broadly and auditory hallucinations specifically are present in several major mental illnesses, including bipolar disorder, post-traumatic stress disorder (PTSD), and most notably schizophrenia spectrum illnesses. Auditory hallucinations involve hearing voices and other sounds when such sounds are not objectively present.

One objective in treating schizophrenia and other illnesses involving psychosis is to provide medication which can obviate the symptoms and allow those suffering with the condition to live in the community. However, because of the complexity of psychosis and the fact that psychiatry remains an inexact science, medications are not always completely effective and can, for a substantial number of sufferers, only partially treat distressing auditory hallucinations or be entirely ineffective in that area.

If a medication regimen is not effective, or if a patient is non-adherent to the regimen, or if titration or medication adjustment is required, symptoms such as hallucinations may remain present, and may impede community functioning and quality of life for the patient. At a minimum, this is information that should be brought to the attention of the person(s) providing treatment, and the occurrence of acute auditory hallucinatory episodes may also indicate a serious worsening of the condition that places the patient and/or others in the community at risk. However, the nature of psychosis makes it very difficult for a patient to "self diagnose" auditory hallucinations.

SUMMARY

According to the present disclosure, a tool is described for supporting an individual suffering from a mental condition or disorder characterized by auditory hallucination.

In one aspect, the present disclosure is directed to a method for supporting an individual suffering from a mental condition or disorder characterized by auditory hallucination in training the individual in distinguishing between an acute auditory hallucinatory episode and ambient sounds. The method comprises monitoring, by at least one processor of a computing device, for a deliberate overt activation action by a user. The activation action represents an indication that the user is hearing sounds, and causes the at least one processor to receive a perception indication from the user. The perception indication is either an indication that the user perceives that they are hearing actual sounds, or an indication that the user perceives that they are experiencing an auditory hallucination. The method then uses at least one microphone on the computing device to monitor ambient sounds; these ambient sounds are tested against a threshold, and recorded as correct or incorrect. The processor(s) record the perception indication as correct where one of the following is true:

the perception indication is an indication that the user perceives that they are experiencing an auditory hallucination and the at least one processor determines that the ambient sounds fail to satisfy the threshold; or the perception indication is an indication that the user perceives that they are hearing actual sounds and the at least one processor determines that the ambient sounds satisfy the threshold.

The processor(s) record the perception indication as incorrect where one of the following is true:

the perception indication is an indication that the user perceives that they are experiencing an auditory hallucination and the at least one processor determines that the ambient sounds satisfy the threshold; or the perception indication is an indication that the user perceives that they are hearing actual sounds and the at least one processor determines that the ambient sounds fail to satisfy the threshold.

In one implementation, the ambient sounds are tested against the threshold locally on the computing device. In another implementation, the ambient sounds are tested against the threshold remotely by transmitting the ambient sounds from the computing device to a remote computer system and receiving threshold testing results from the remote computer system at the computing device.

The processor(s) may further generate a report indicating correctness of a prior series of perception indications. The report may further comprise recommendations for improving discrimination between auditory hallucinations and ambient sounds, and/or accuracy trends for the perception indications to monitor progress of the user over time.

The perception indication may be subsumed within the activation action.

The threshold may be a minimum confidence level associated with voice activity detection of the ambient sounds.

In another aspect, the present disclosure is directed to a computing device comprising at least one processor, at least one microphone coupled to the at least one processor, at least one input device coupled to the at least one processor, and at least one memory coupled to the at least one processor, the memory containing instructions which, when executed by the at least one processor, cause the at least one processor to implement the above-described method for supporting an individual suffering from a mental condition or disorder characterized by auditory hallucination in training the individual in distinguishing between an acute auditory hallucinatory episode and ambient sounds.

In yet another aspect, the present disclosure is directed to a tangible computer-readable medium containing computer-usable instructions for execution by at least one processor of a computing device, wherein the instructions, when executed by the at least one processor, cause the at least one processor to implement the above-described method for supporting an individual suffering from a mental condition or disorder characterized by auditory hallucination in training the individual in distinguishing between an acute auditory hallucinatory episode and ambient sounds.

BRIEF DESCRIPTION OF THE DRAWINGS

These and other features of the invention will become more apparent from the following description in which reference is made to the appended drawings wherein:

FIG. 3 shows an illustrative structure for an illustrative function for capturing the amplitude of audio;

FIG. 4 shows an illustrative structure for an illustrative function for building a sine waveform based on detected amplitude;

FIG. 5 shows an illustrative structure for an illustrative function for applying detected sound to a waveform;

DETAILED DESCRIPTION

Figure 1:
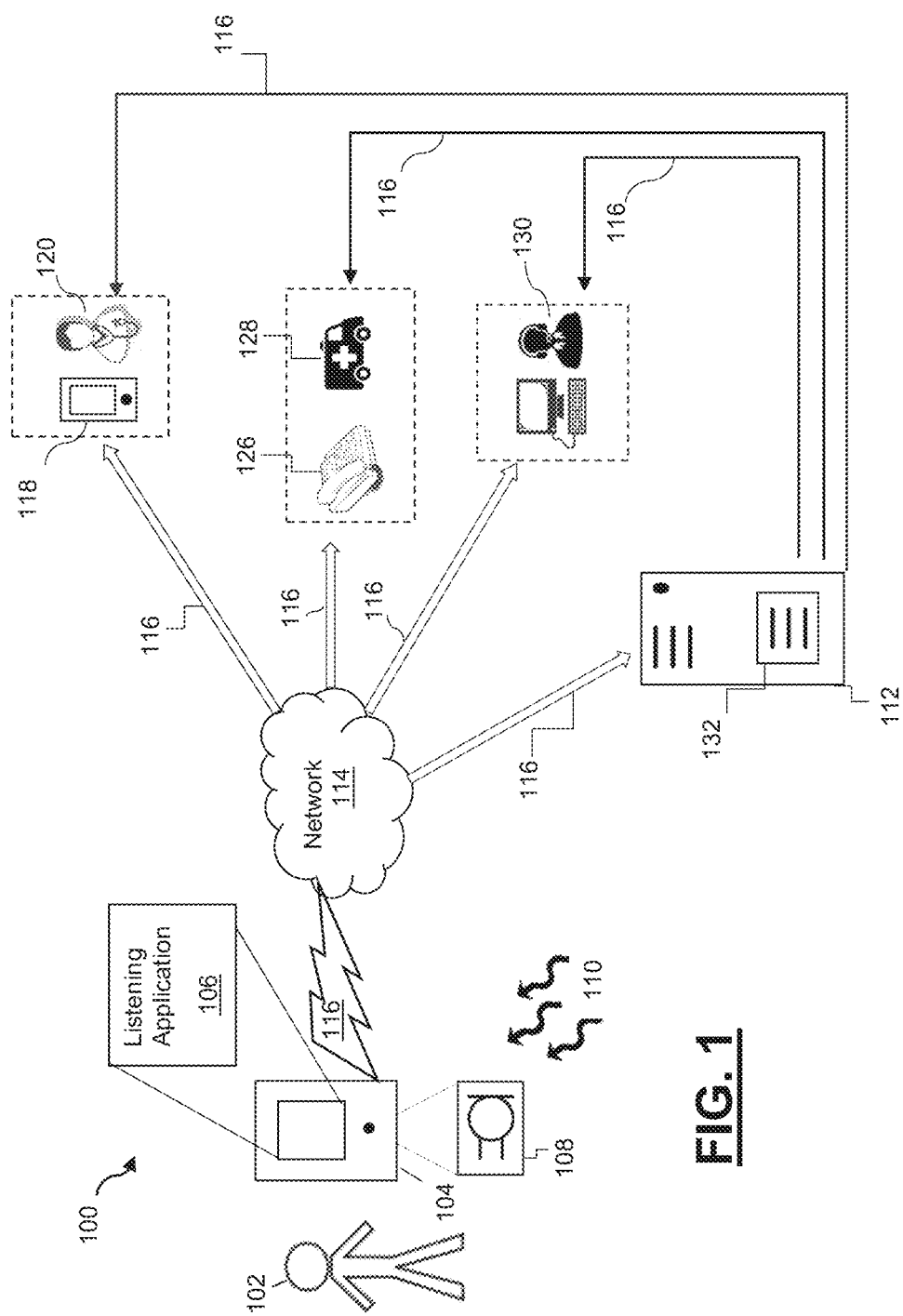
FIG. 1 shows in schematic form an illustrative system for providing a remote alert signal identifying potential occurrence of an acute auditory hallucinatory episode and supporting an individual suffering from a mental condition or disorder characterized by auditory hallucination in training the individual in distinguishing between an acute auditory hallucinatory episode and ambient sounds.

Reference is now made to FIG. 1, which shows in schematic form an illustrative system, indicated generally by reference 100, for supporting an individual suffering from a mental condition or disorder characterized by auditory hallucination. The system 100 can support training the individual in distinguishing between an acute auditory hallucinatory episode and ambient sounds, and can provide a remote alert signal identifying potential occurrence of an acute auditory hallucinatory episode.

A first networked mobile wireless telecommunication computing device, represented for simplicity of illustration by smartphone 104, is associated with a user 102 who has been diagnosed with psychosis. The smartphone 104 may be owned by the user 102, or merely possessed by the user 102 under a loan, lease, bailment or other suitable arrangement. The smartphone 104 is merely one representative example of a networked mobile wireless telecommunication computing device, which may also be a tablet, smartwatch or other suitable device possessing a microphone, suitable wireless communication hardware and sufficient processing capacity. The wireless communication hardware may operate in conjunction with other communication hardware, for example a WiFi signal from a smartwatch or tablet may communicate with a router having a wired connection to one or more networks.

The processor(s) of the smartphone 104 execute a listening application 106, which monitors for a deliberate overt activation action by the user 102. Importantly and critically, the activation action represents an affirmative, unambiguous indication by the user that the user 102 is hearing voices or other sounds. For example, the listening application 106 may have a virtual button on a screen thereof that says "I'm hearing things" or "I am hearing voices" or "Are the voices real?" or "Discretely check the background for noises", or something similar. Alternatively, the listening application 106 may have an activation action that involves a specific sequence of button pushes, or a specific gesture, such as vigorously shaking the smartphone 104 in a manner that can be unambiguously be detected by an onboard accelerometer. The listening application 106 may run in the background for rapid access, or may be launched when needed. In the latter case, the act of launching the listening application 106 may represent an affirmative, unambiguous indication by the user that the user 102 is hearing sounds. The listening application 106 may be a stand-alone application, or may be a component of a larger software application providing additional features and functionality, for example to assist an individual with psychosis with living in the community.

In some embodiments, as described further below in the context of FIG. 2A, the processor(s) executing the listening application 106 on the smartphone 104 may also receive a perception indication from the user. The perception indication is either an indication that the user perceives that they are hearing actual sounds, or an indication that the user perceives that they are experiencing an auditory hallucination. The perception indication may be provided as a separate step, or the perception indication may be subsumed within the activation action. For example, with separate steps the overt activation action may be pressing an on-screen button that says "I am hearing sounds" and the perception indication may be provided by pressing one of two on-screen buttons, where one button says "I think these are real sounds" and the other button says "I think I am hallucinating". In a combination there may simply be the two on-screen buttons that say, respectively, "I think these are real sounds" and "I think I am hallucinating" or words to that effect; pressing either button necessarily implies an indication that the user is hearing sounds such that the perception indication is subsumed within the activation action.

In response to the activation action by the user 102, the processor(s) executing the listening application 106 on the smartphone 104 uses at least one microphone 108 on the smartphone 104 to monitor ambient sounds, shown as arrows 110. In some embodiments, the microphone 108 may be inactive prior to the activation action, so that only ambient sounds 110 after the activation action are monitored. In other embodiments, the processor(s) executing the listening application 106 may cause the microphone 108 to remain active in the background. For example, the processor(s) executing the listening application 106 may continuously record ambient sounds 110 and store a predetermined duration (e.g. a preceding 5 seconds, 10 seconds, etc.) thereof in a rolling buffer so that ambient sounds 110 immediately prior to the activation action may be used, either alone or in addition to ambient sounds 110 following the activation action.

Optionally, the listening application 106 may display a waveform or other representation of the ambient sounds 110 on a screen of the smartphone 104.

The processor(s) executing the listening application 106 test the ambient sounds 110 against a threshold to determine whether the user 102 is experiencing an acute auditory hallucinatory episode. The threshold is designed to test whether evidence present in the ambient sounds 110 supports the perception of the user 102 with respect to actual voices or an auditory hallucination. Depending on the desired bias in terms of Type I error (false positive) vs. Type II error (false negative), various thresholds can be used, alone or in combination. For example, the threshold may be a minimum volume threshold, or may be a minimum confidence level associated with voice activity detection and/or natural language processing of the ambient sounds 110, e.g. whether or not a voice activity detection/natural language processing engine can identify spoken works in the ambient sounds 110. These are merely some representative examples of thresholds, and are not intended to be limiting.

The processor(s) executing the listening application 106 may test the ambient sounds 110 against the threshold locally on the smartphone 104, or remotely by transmitting the ambient sounds 110 from the networked mobile wireless telecommunication computing device to a remote computer system 112 through one or more networks 114 (e.g. comprising one or more wireless networks, intranets, cellular networks, the publically switched telephone network (PSTN) and/or the Internet) to which the smartphone 104 is coupled and receiving threshold testing results from the remote computer system 112 at the smartphone 104. In the latter case, the remote computer system 112 may have far superior processing capacity to the smartphone 104 so as to more rapidly execute the required processing, e.g. voice activity detection and/or natural language processing.

If the processor(s) executing the listening application 106 determine that the ambient sounds 110 fail to satisfy the threshold, this indicates that the ambient sounds 110 detected by the microphone 108 do not support an inference that the sounds heard by the user 102 are actually present, and therefore that the sounds may be an auditory hallucination.

Where the processor(s) executing the listening application 106 on the smartphone 104 also receive a perception indication from the user, the processor(s) may also record the perception indication as either correct or incorrect. The processor(s) will record the perception indication as correct if (a) the perception indication is an indication that the user perceives that they are experiencing an auditory hallucination and the processor(s) determine that the ambient sounds fail to satisfy the threshold; or (b) the perception indication is an indication that the user perceives that they are hearing actual sounds and the processor(s) determine that the ambient sounds satisfy the threshold. The processor(s) will record the perception indication as incorrect if (a) the perception indication is an indication that the user perceives that they are experiencing an auditory hallucination and the processor(s) determine that the ambient sounds satisfy the threshold; or (b) the perception indication is an indication that the user perceives that they are hearing actual sounds and the processor(s) determine that the ambient sounds fail to satisfy the threshold. Optionally, the processor(s) executing the listening application 106 may provide a visual and/or audible notification to the user 102 as to the accuracy of the user's perception of whether the user 102 is hearing actual voices or experiencing an auditory hallucination. This may provide reassurance to the user 102 that the user 102 is correctly distinguishing between actual ambient sounds and auditory hallucination.

After recording the perception indication (where one is received) as either correct or incorrect, the processor(s) executing the listening application 106 on the smartphone 104 may generate a report, which may be presented to the user and/or sent to personnel involved in treating and/or supporting the user 102, such as by transmission to a second networked mobile wireless telecommunication computing device 118 associated with a medical professional 120.

As noted above, if the processor(s) executing the listening application 106 determine that the ambient sounds 110 fail to satisfy the threshold, this indicates that the ambient sounds 110 detected by the microphone 108 do not support an inference that the sounds heard by the user 102 are actually present, and therefore that the sounds may be an auditory hallucination. Accordingly, responsive to the processor(s) executing the listening application 106 determining that the ambient sounds fail to satisfy the threshold, the processor(s) executing the listening application 106 may cause the smartphone 104 to wirelessly transmit one or more alert signals 116 that identify the user 102 and indicate that the user 102 may be experiencing an auditory hallucination. Optionally, where the perception indication is correct, i.e. the user 102 has correctly perceived that they are experiencing an auditory hallucination, the processor(s) executing the listening application 106 may not send the alert signal(s) 116. Thus, the alert signal(s) 116 may be sent only where the user experiences an auditory hallucination and incorrectly identifies it as actual sounds. The alert signal(s) 116 are sent, via the network(s) 114, to at least one remote receiving device beyond the smartphone 104. Examples of remote receiving devices include at least one second networked mobile wireless telecommunication computing device 118 associated with a medical professional 120 involved in treatment of the user 102, a telephone or dispatch system 126 associated with an ambulance or paramedic service 128, and a dedicated monitoring center 130. The alert signal(s) 116 can be one or more of a text message, a pager message, a telephone call, an e-mail message, a push notification or other types of signal. The alert signal(s) 116 may indicate that the user 102 may be experiencing an auditory hallucination either explicitly, or implicitly (e.g. a push notification on a dedicated application running on a smartphone or other device associated with a medical professional 120 involved in treatment of the user 102).

The processor(s) may cause transmission of the alert signal 116 in response to a single instance for which the processor(s) determines, in response to the activation action, that the ambient sounds fail to satisfy the threshold. In other embodiments, the alert signal(s) 116 will only be generated after a predetermined number of instances within a predetermined time period for which, following an activation action by the user 102, the processor(s) executing the listening application 106 determine that the ambient sounds 110 fail to satisfy the threshold. Additionally, in some embodiments, the number of activation actions by the user, and the number of times that the ambient sounds 110 fail to satisfy the threshold, may be recorded and transmitted to inform clinicians of patient wellness between appointments.

As noted above, the smartphone 104 is merely one representative example of a networked mobile wireless telecommunication computing device. Where the device (e.g. smartphone 104) has telephone connectivity through the network(s) 114, the alert signal 116 may be, for example, an automated telephone call, text message, pager message or e-mail message sent according to conventional protocols. Alternatively, the alert signal 116 may be transmitted through the network(s) 114 to another system, e.g. remote computer system 112, for further processing. For example, profile information 132 about the user 102 may be stored on the remote computer system 112, and the remote computer system 112 can use the profile information 132 to embellish the alert signal 116. For example, the alert signal 116 may consist of a unique identifier for the user 102, or a limited data set (e.g. a unique identifier and timestamp and/or location). The remote computer system 112 can forward the embellished alert signal 116, which can then be forwarded to, for example, one or more of a device 118 associated with a medical professional 120 involved in treatment of the user 102, a telephone or dispatch system 126 associated with an ambulance or paramedic service 128, and a dedicated monitoring center 130. Alternatively or additionally, the remote computer system 112 may update an electronic medical record of the user 102 based on the alert signal 116. The alert signal 116 may trigger an alert within the electronic medical record and/or an alarm on a web portal.

Optionally, where available, the alert signal 116 can include location information (e.g. from a location processor of the smartphone 104). For example, if a profile of the user 102 indicates that he or she may pose a danger to himself/herself or others in the event of auditory hallucinations, the alert signal 116 can be used to dispatch emergency medical personnel 128 to the location of the smartphone 104, which is expected to be at (or at least near) the location of the user 102. In such cases, the alert signal can also provide additional information, such as one or more photographs of the user 102 to assist emergency medical personnel 128 in identifying the user 102 when they arrive.

Figure 2:
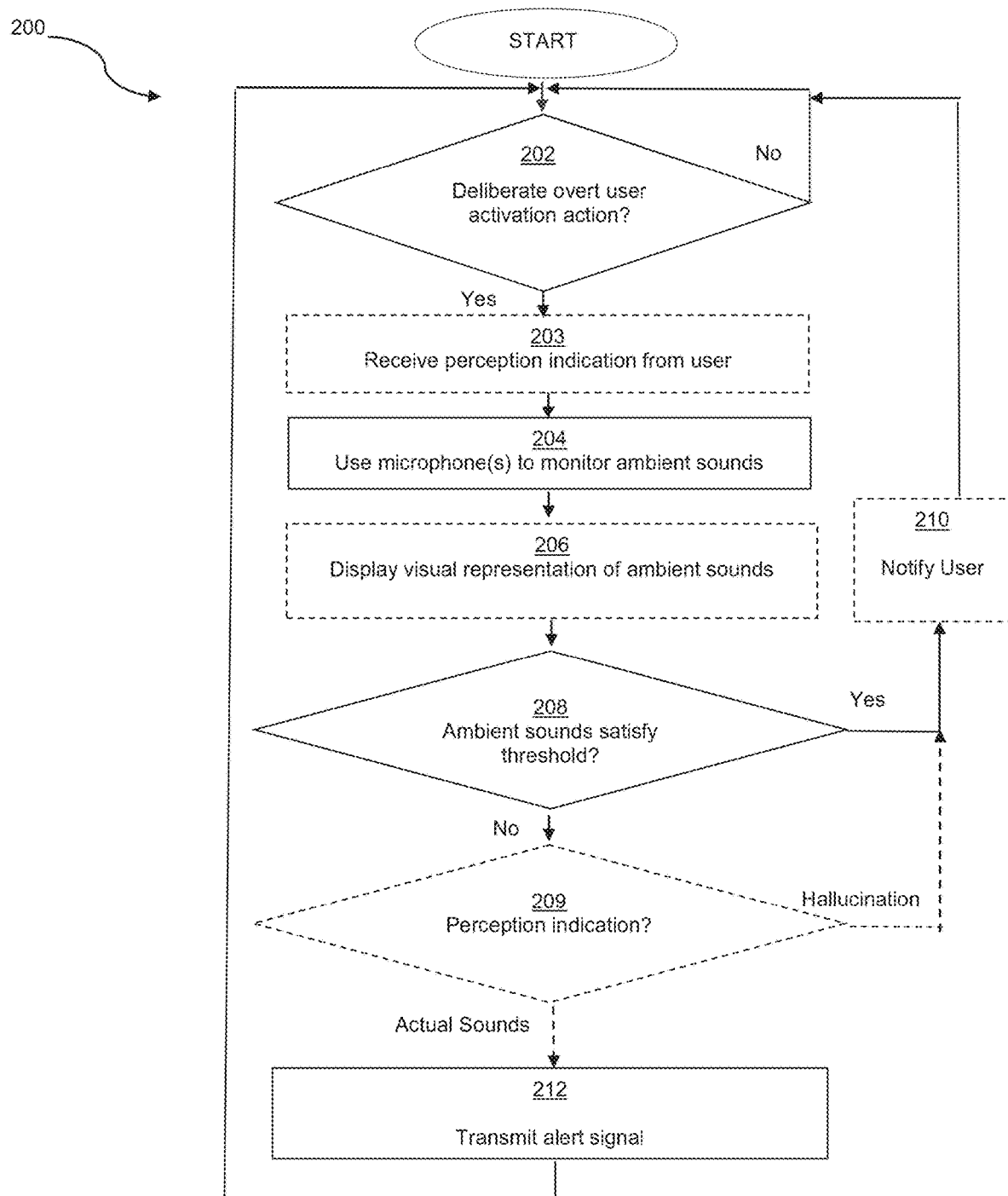
FIG. 2 is a flow chart showing an illustrative method for providing a remote alert signal identifying potential occurrence of an acute auditory hallucinatory episode.

Reference is now made to FIG. 2, in which an illustrative method for providing a remote alert signal identifying potential occurrence of an acute auditory hallucinatory episode is indicated generally at reference 200.

At step 202, the method 200 monitors, by at least one processor of a first computing device, for a deliberate overt activation action by a user. As noted above, the activation action, when detected, represents an indication that the user is hearing sounds. If the activation action is detected (a "yes" at step 202), the method 200 proceeds to optional step 203 to receive a perception indication and then to step 204; otherwise (a "no" at step 202) the method 200 continues to monitor at step 202.

At step 204, responsive to the activation action being detected, the processor(s) using at least one microphone on the first computing device to monitor ambient sounds. In one illustrative implementation, the Cordova-Plugin-Media sound detector, available from Apache for both Android and iOS platforms at https://cordova.apache.org/docs/en/latest/reference/cordova-plugin-media/, may be used to access the microphone. This package allows the microphone to capture any ambient sounds around the computing device, and to play, pause and stop recorded audio, change the volume and read the current position of playing audio. In one illustrative embodiment, ambient sounds are captured by the interval function (shown below) every 0.4 seconds. The amplitude range is 0 to 1, with voice capture sensitivity set to anything more than 0.06 of the amplitude rate to eliminate very low volume noises. This is merely one illustrative implementation and is not limiting.

The function for capturing the amplitude of audio in the Cordova-Plugin-Media is: media.getCurrentAmplitude(mediaSuccess, [mediaError]);. The structure shown at reference 300 in FIG. 3 is used to implement this function.

Returning to FIG. 2, after step 204 the method 200 proceeds to optional step 206, where the processor(s) may display a visual representation of the ambient sounds on a display of the first computing device. In one illustrative implementation, the ambient sounds are visualized as a sine waveform (other visual representations may also be used). A first function, shown at 400 in FIG. 4, may be used to build the sine waveform based on detected amplitude. The amplitude is magnified to enable identification of minor changes in the wave form. The sine curve is drawn in 10 px segments starting at the origin in this function. The height of the sine waveform is changing based on detected sound amplitude with a parameter called "unit". This allows the waveform to be plotted on a display of the first computing device. The detected sound may then be applied to the waveform using the function shown at 500 in FIG. 5, according to the following recursive steps:

1. Clear the screen in position (x, y) with context.clearRect;
2. Save cleared screen;
3. Define color and width of waveform;
4. Draw sine curve at moment of t;
5. Update moment of t; and
6. Return to step (1).

After optional step 206, or from step 204 where optional step 206 is omitted, the method 200 proceeds to step 208, where the processor(s) test the ambient sounds against a threshold. As noted above, this may be done locally or remotely, and the threshold may be, for example, a minimum volume threshold, a minimum confidence level associated with voice activity detection and/or natural language processing of the ambient sounds, or another suitable threshold.

If the processor(s) determine at step 208 that the ambient sounds satisfy the threshold (a "yes" at step 208), this indicates that the ambient sounds detected by the microphone supporting an inference that the sounds heard by the user are actually present, and the method proceeds to optional step 210 to provide a visual and/or audible notification to the user, and then returns to step 202.

If the processor(s) determine at step 208 that the ambient sounds fail to satisfy the threshold (a "no" at step 208), this indicates that the ambient sounds detected by the microphone(s) do not support an inference that the sounds heard by the user are actually present, and therefore that the sounds may be an auditory hallucination. At optional step 209, the method 200 checks whether the perception indication was correct, that is, whether the user 102 perceived that they were experiencing an auditory hallucination. Responsive to the processor(s) determining that the ambient sounds fail to satisfy the threshold (a "no" at step 208) and optionally that the user 102 did not correctly perceive that they were experiencing an auditory hallucination ("actual sounds" at optional step 209), the method 200 proceeds to step 212. At step 212, the processor(s) transmit an alert signal, via a network to which the first computing device is coupled, to at least one remote receiving device beyond the first computing device. The alert signal may be transmitted, for example, in the manner described above. After step 212, the method 200 returns to step 202, or may optionally end.

In addition to providing an alert signal if the ambient sounds detected by the microphone(s) indicate an auditory hallucination, the present disclosure also describes methods for supporting an individual in learning to distinguish between auditory hallucinations and actual ambient sounds.

Figure 2A:
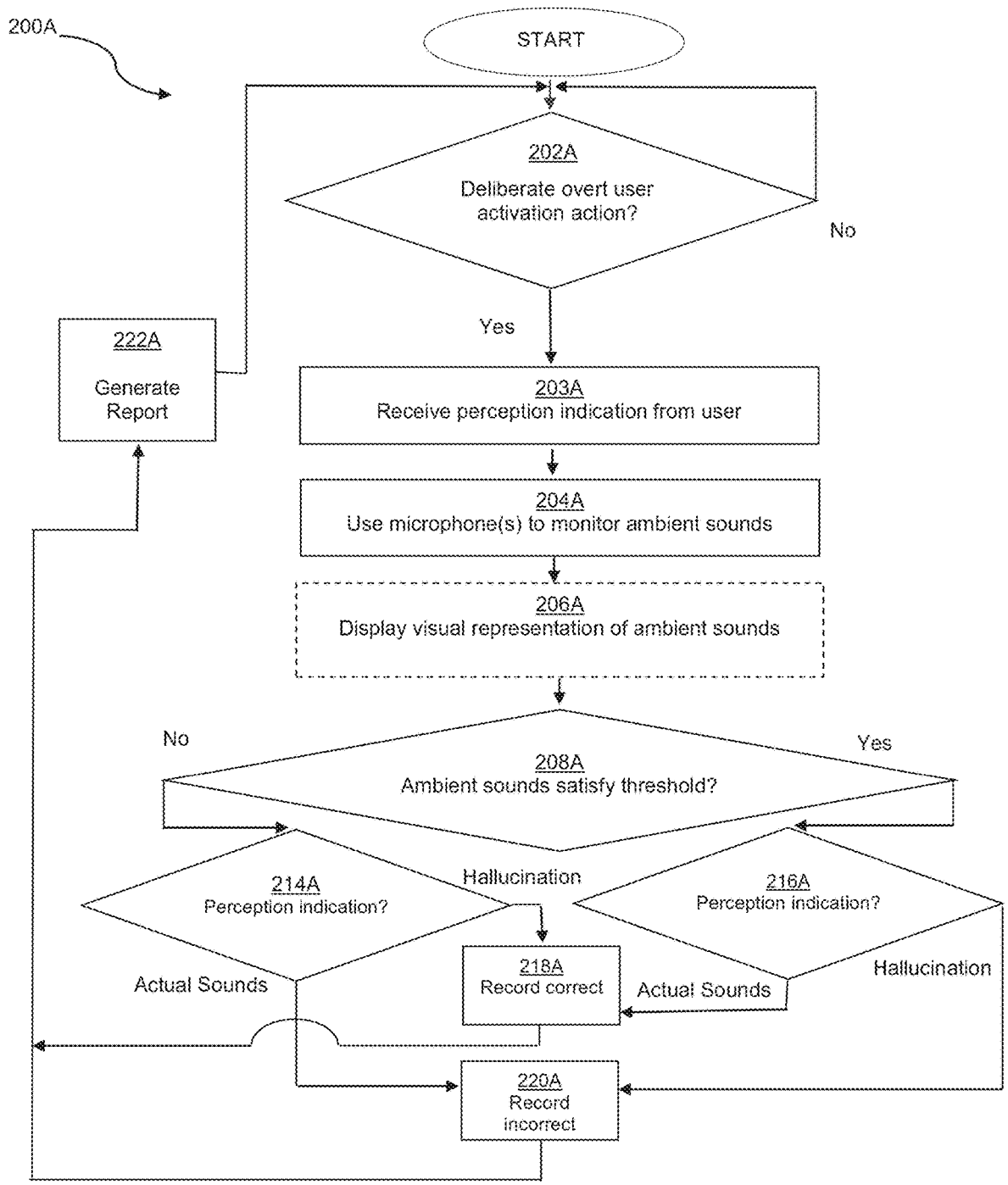
FIG. 2A is a flow chart showing an illustrative method for supporting an individual suffering from a mental condition or disorder characterized by auditory hallucination in training the individual to distinguish between an acute auditory hallucinatory episode and ambient sounds.

Reference is now made to FIG. 2A, which shows an illustrative method 200A for supporting an individual suffering from a mental condition or disorder characterized by auditory hallucination. The method 200A provides support in training the individual to distinguish between an acute auditory hallucinatory episode and ambient sounds, and may be used in combination with, or separately from, the method 200 shown in FIG. 2, and may be implemented by the listening application 106. The method 200A is preferably implemented using a networked computing device (e.g. wired or wireless), and more preferably implemented using a networked mobile wireless telecommunication computing device such as a smartphone, so as to additionally enable the functionality of the method 200 shown in FIG. 2. However, the method 200A shown in FIG. 2A is not so limited, and may be implemented on any suitable microphone-equipped computing device, including a computing device with no network connection (i.e. an isolated or "air gapped" computing device). Moreover, the microphone need not be integral to the computing device, but may also be a peripheral microphone that is releasably communicatively coupled to the computing device. Thus, references to a microphone being "on" a computing device should be understood as including a releasable peripheral microphone that is releasably communicatively coupled to the computing device.

At step 202A, the method 200A monitors, by at least one processor of a first computing device, for a deliberate overt activation action by a user. As before, the activation action represents an indication that the user is hearing sounds.

At step 203A, responsive to the activation action being detected, the method 200A causes the processor(s) to receive a perception indication from the user. The perception indication received at step 203A is either an indication that the user perceives that they are hearing actual sounds, or an indication that the user perceives that they are experiencing an auditory hallucination. Steps 202A and 203A may be presented as separate steps as shown, or may be combined into a single step in which the perception indication is subsumed within the activation action. For example, with separate steps the overt activation detected at step 202A may be pressing an on-screen button that says "I am hearing sounds" and the perception indication received at step 203A may be pressing one of two on-screen buttons, where one button says "I think these are real sounds" and the other button says "I think I am hallucinating". In a combination of steps 202A and 203A, there may simply be the two on-screen buttons that say, respectively, "I think these are real sounds" and "I think I am hallucinating" or words to that effect; pressing either button necessarily implies an indication that the user is hearing sounds such that the perception indication is subsumed within the activation action.

After step 203A, at step 204A the method 200A causes the processor(s) to use at least one microphone on the first computing device to monitor ambient sounds. In one illustrative implementation, the Cordova-Plugin-Media sound detector, available from Apache for both Android and iOS platforms at https://cordova.apache.org/docs/en/latest/reference/cordova-plugin-media/, may be used to access the microphone, as described above.

Next, at optional step 206A, the processor(s) may display a visual representation of the ambient sounds on a display of the first computing device, as described above.

After optional step 206A, or from step 204A where optional step 206A is omitted, the method 200A proceeds to step 208A, where the processor(s) test the ambient sounds against a threshold. As noted above, this may be done locally on the first computing device or remotely by transmitting the ambient sounds from the first computing device to a remote computer system and receiving threshold testing results from the remote computer system.

The threshold may be, for example, a minimum volume threshold, a minimum confidence level associated with voice activity detection and/or natural language processing of the ambient sounds, or another suitable threshold. Preferably, in the method 200A the threshold is a minimum confidence level associated with voice activity detection of the ambient sounds.

Based on the outcome of step 208A, the method 200A causes the processor(s) to record the perception indication as either correct or incorrect. The processor(s) will record the perception indication as correct (step 218A) if the perception indication is an indication that the user perceives that they are experiencing an auditory hallucination ("hallucination" at step 214A) and the processor(s) determine that the ambient sounds fail to satisfy the threshold ("no" at step 208A). The processor(s) will also record the perception indication as correct (step 218A) if the perception indication is an indication that the user perceives that they are hearing actual sounds ("actual sounds" at step 216A) and the processor(s) determine that the ambient sounds satisfy the threshold ("yes" at step 208A). The processor(s) will record the perception indication as incorrect (step 220A) where the perception indication is an indication that the user perceives that they are experiencing an auditory hallucination ("hallucination" at step 216A) and the processor(s) determine that the ambient sounds satisfy the threshold ("yes" at step 208A). The processor(s) will record the perception indication as incorrect (step 220A) where the perception indication is an indication that the user perceives that they are hearing actual sounds ("actual sounds" at step 214A) and the processor(s) determine that the ambient sounds fail to satisfy the threshold ("no" at step 208A). While FIG. 2A shows step 208A preceding steps 214A and 216A, in other embodiments the order may be reversed wherein the method may equivalently apply a threshold test dependent on whether or not the perception indication is an indication that the user perceives that they are hearing actual sounds or an indication that the user perceives that they are experiencing an auditory hallucination.

After recording the perception indication as either correct (step 218A) or incorrect (step 220A), the method 200A proceeds to step 222A, where the processor(s) will generate a report indicating correctness of a prior series of perception indications and present that report to the user. The series may be a series of one, that is, only the most recent perception indication, or a larger series (e.g. the past two, five, ten, twenty or any arbitrary number of perception indications). The report generated at step 222A may also comprise recommendations for improving discrimination between auditory hallucinations and ambient sounds, accuracy trends for the perception indications to monitor progress of the user over time, or both. The recommendations may be based on an analysis of the types of errors in perception indications. For example, different recommendations may be provided to a user who is more likely to mistake hallucinations for real sounds than to a user who is more likely to mistake real sounds for hallucinations. Thus, the recommendations may be tailored based on the user's performance.

Optionally, the report generated at step 222A, or a log indicating correctness of the prior series of perception indications, may be transmitted to one or more healthcare professionals treating or supporting the user.

After step 222A, the method 200A returns to step 202A or alternatively may end.

FIGS. 8A through 8F show illustrative user interface screens 800 for a networked mobile wireless telecommunication computing device implementing aspects of the methods 200, 200A described herein.

Figure 8A:
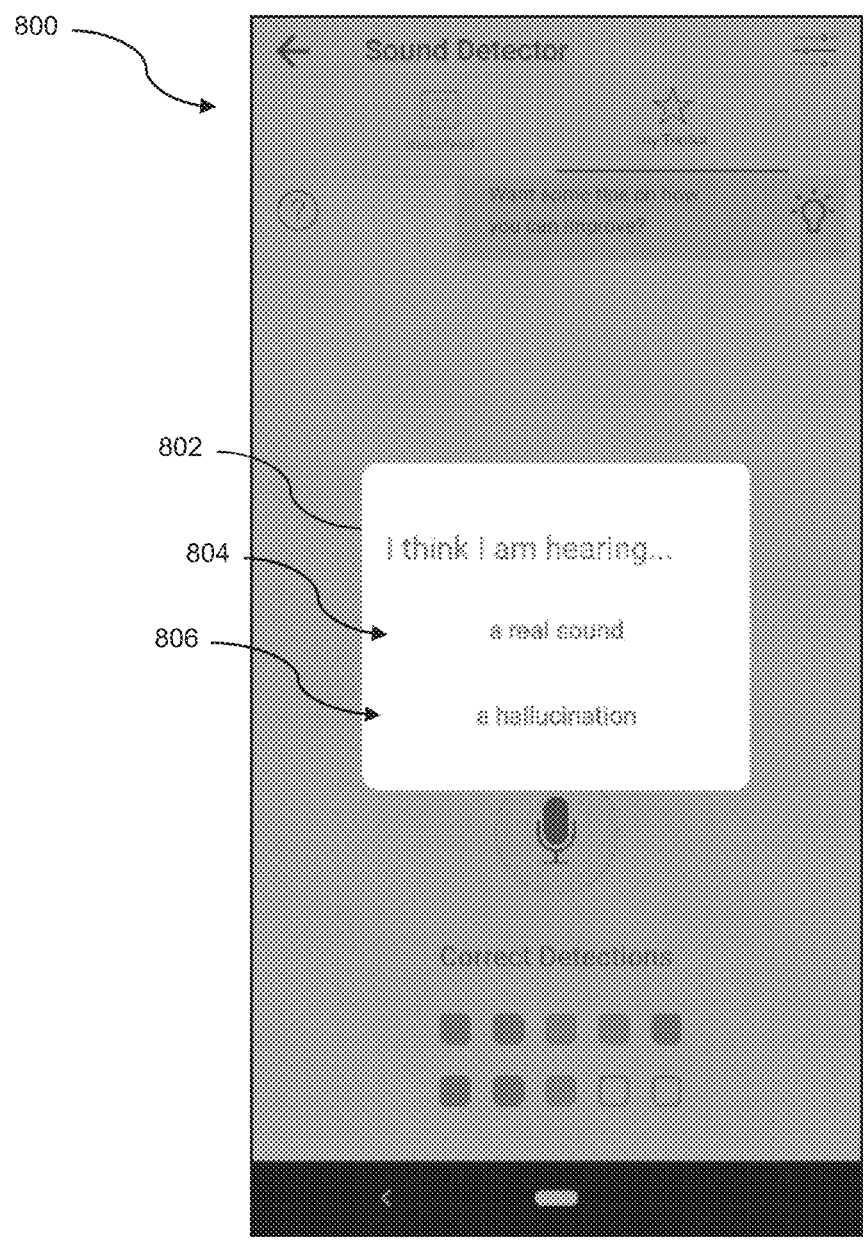
FIGS. 8A through 8F show illustrative user interface screens for a computing device implementing aspects of the methods described herein.

FIG. 8A shows an illustrative user interface screen 800 implementing a combination of steps 202A and 203A. There is a box 802 that states "I think I am hearing . . . " with two on-screen buttons 804, 806. The first on-screen button 804 says "a real sound" and the second on-screen button 806 says "a hallucination". Pressing either button necessarily implies an indication that the user is hearing sounds; pressing the first button 804 is an indication that the user perceives that they are hearing actual sounds and pressing the second button 806 is an indication that the user perceives that they are experiencing an auditory hallucination.

Figure 8B:
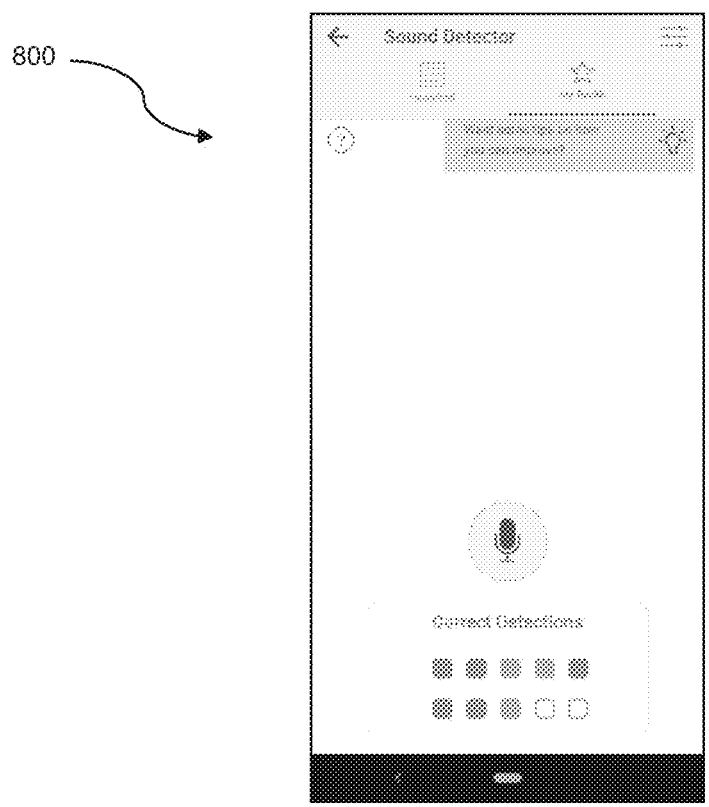
Figure 8C:
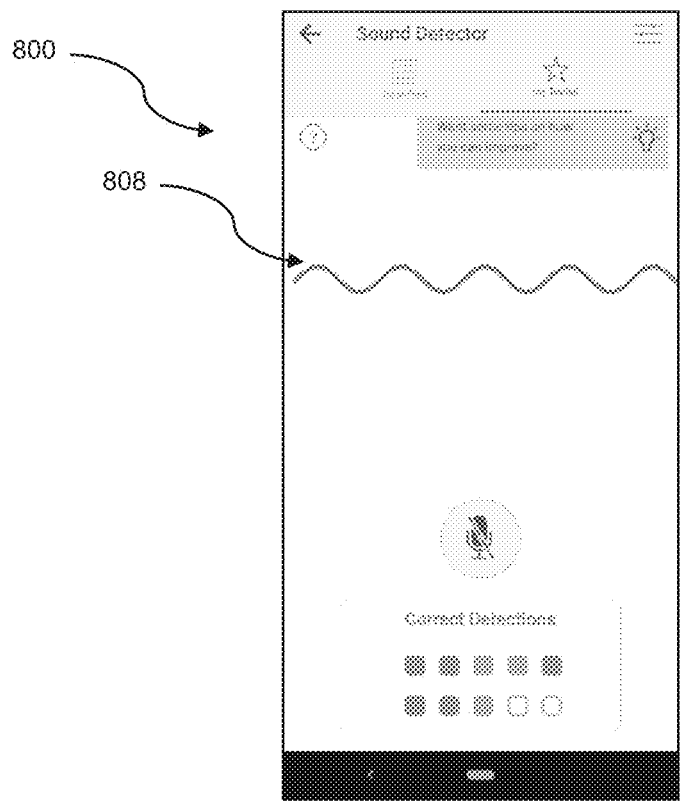

FIGS. 8B and 8C show illustrative user interface screens 800 for steps 204A and 206A, respectively. In FIG. 8C, the user interface screen 800 displays a waveform 808 representing ambient sounds.

Figure 8D:
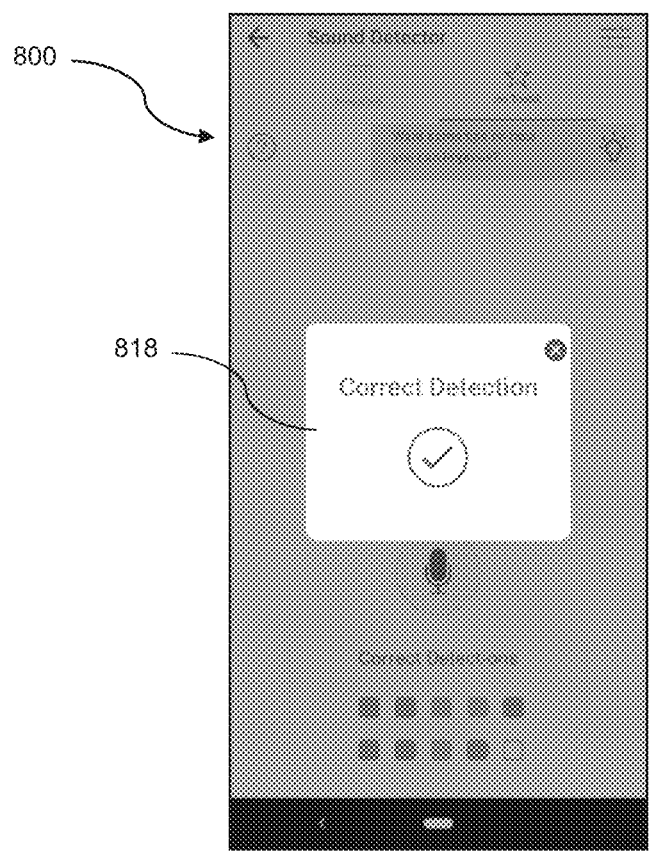
Figure 8E:
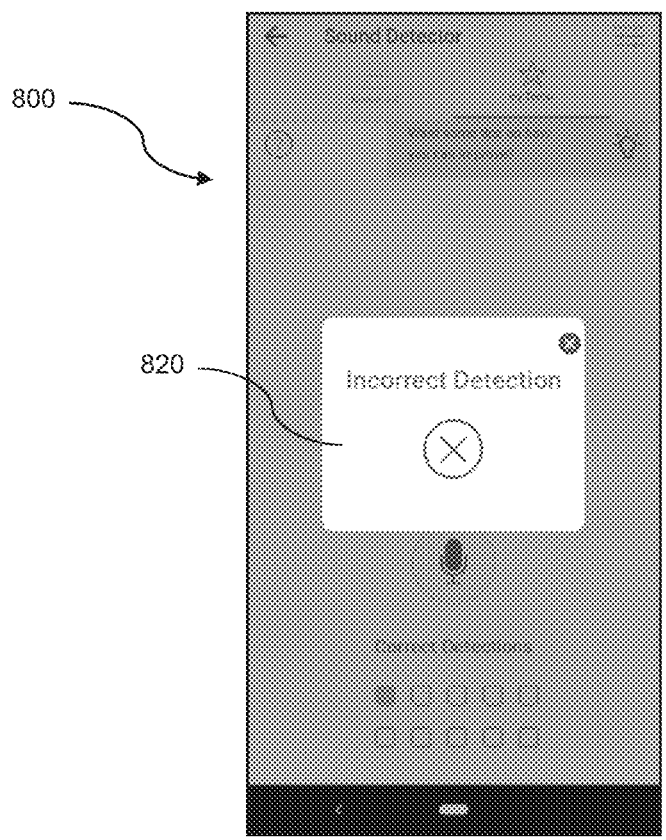

FIGS. 8D and 8E show illustrative user interface screens 800 for steps 218A and 220A, respectively. The user interface screen 800 in FIG. 8D presents a box 818 indicating that the perception indication was recorded as correct at step 218A. Conversely, the user interface screen 800 in FIG. 8E presents a box 820 indicating that the perception indication was recorded as incorrect at step 220A.

Figure 8F:
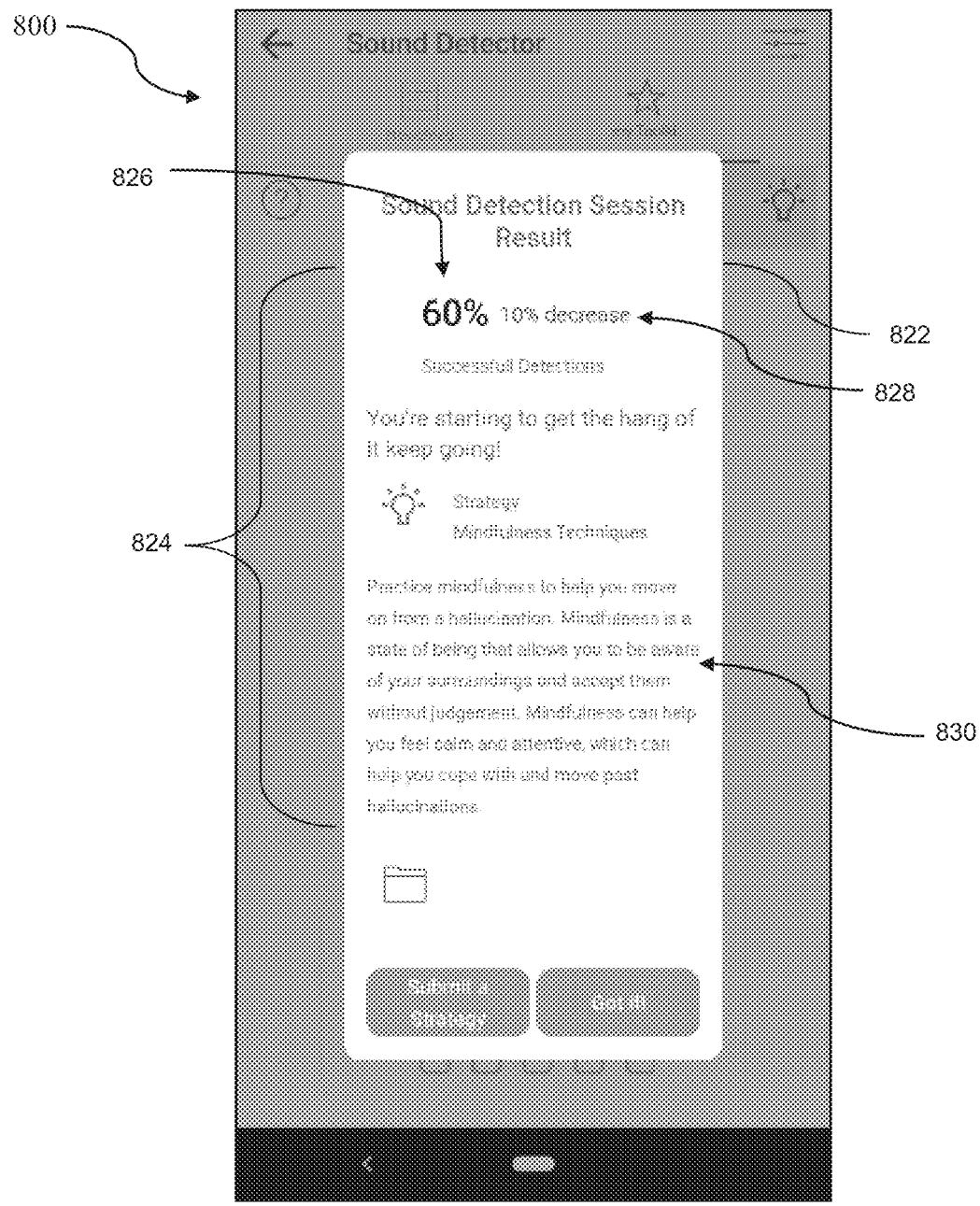

FIG. 8F shows an illustrative user interface screen 800 implementing step 222A, and presents a box 822 containing the report 824. The report 824 includes an indication 826 of the correctness of a prior series of perception indications, an accuracy trend 828 and recommendations 830 for improving discrimination between auditory hallucinations and ambient sounds.

As noted above, in the method 200A the threshold used at step 208A is preferably a minimum confidence level associated with voice activity detection of the ambient sounds. The purpose is to identify the presence of human voices speaking and discriminate between ambient noise and human voices, specifically speech. This is referred to as voice activity detection. The objective is to help the user distinguish between audio hallucinations (voices being heard internally/in their head) and background human speech or voices in an adjacent room or area when another person present or nearby may not be visible.

Thus, at step 204 or 204A, the method 200, 200A will record a sampling of the ambient sound within a given timeframe. Steps 208, 208A may then use computational analysis to determine the presence or absence of human speech in the audio sample. In one embodiment, a machine learning model may be built using a training set of raw audio signals, which are captured from similar environments as would be expected during real world use and that have been pre-processed and broken down into frames. Features can be engineered from the frames for each data sample with a labelled outcome and used in training a classifier (e.g. support vector machine, neural net, etc.) that will be able to determine the outcome of the sample—being either voiced speech, unvoiced speech, or silence. The model can then be tuned and tested on unseen data to evaluate its performance level, and then beta tested.

The process of classifying unseen (new) audio data may occur either on the computing device itself or, in the case of a networked computing device, may be transmitted to a cloud based/networked computer for analysis of the sample. The resulting computational analysis may also partially take place onboard (within the computing infrastructure of the networked computing device) and externally on another networked device (the cloud). The resulting analysis will calculate the likelihood of the presence of human speech within the sample.

The process may or may not require a calibration function to initially reduce the level of ambient noise and to calculate the thresholds for speech detection. Such a calibration process would require steps such as reducing the level of ambient noise (commonly done via spectral subtraction) and then calculating essential features of the sound (specifically the energy thresholds of the audio samples). These essential features of the sound can then be classified. (The term "essential" here refers solely to sound features and should not be used in construing the claims.)

The statistical analysis and classification of energy signals within audio files remains the most complex step of voice activity detection, and several subtypes of statistics are commonly used. These include:

Spectral Slope (based on energy change between different audio frequencies within audio spectra)

Correlation Coefficients

Log likelihood ratio

Cepstrum: takes inverse Fourier transform of log(spectrum)

Modified distance

Several frameworks may be applied to voice activity detection. It is to be noted that some or all of the frameworks may be subject to copyright restrictions, patent restrictions, open source license restrictions or other restrictions, and nothing in this document is to be construed as authorizing the use of such frameworks without all necessary permissions. Each of the voice activity frameworks described below is incorporated herein by reference.

One illustrative framework is G.729. Although this is an older algorithm that has largely been surpassed in performance, it remains a workable solution and serves as a performance reference point for newer voice activity detection protocols. One implementation in MATLAB is available at: https://www.mathworks.com/help/dsp/examples/g-729-voice-activity-detection.html Another illustrative framework is the WebRCT voice activity detector. This is a Google-developed API primarily for web-based communication, and includes a built-in voice activity detection. While this may not be an ideal approach given the need for local execution, the source code is available and could be adapted. An implementation is available at: https://pypi.org/project/webrtcvad/.

ETSI VAD is another older algorithm that may be used as a performance standard (like G.729), and a document that explains aspects of classification and noise adjustment is listed at https://www.etsi.org/deliver/etsi_i_ets/300700_300799/300730/01_20_103/ets_300730e01c.pdf.

An illustrative adaptive energy based framework is available at the following website: http://citeseerx.ist.psu.edu/viewdoc/download?doi=10.1.1.176.6740&rep=rep1&type=pdf.

Neural network based approaches may also be applied to voice activity detection. One example is found at https://ieeexplore.ieee.org/stamp/stamp.jsp?arnumber=8278160.

There are also a number of python libraries for manipulating speech, listed under the heading VoiceBook, at https://github.com/jim-schwoebel/voicebook. There are several Github libraries similar to VoiceBook, which stretch across different languages. One called SpeechRecognition includes an ambient noise adjustment function, which takes a period during which speech is absent, collects its energy threshold, and subtracts this from the voice recording. It is available at: https://github.com/Uberi/speech_recognition/blob/master/speech_recognition/_init_.py Other projects listed on GitHub use a variety of techniques to distinguish speech from ambient noise. The simplest applications use spectral subtraction (of the ambient noise pattern from the full audio file), but some use more complex methods, like trained neural networks and high-level statistics. Most of the raw code made available has been written in python.

These include those listed at:
https://github.com/eesungkim/Voice_Activity_Detector
https://github.com/jtkim-kaist/VAD
https://github.com/wahibhaq/android-speaker-audio-analysis/tree/master/Android
https://github.com/shriphani/Listener While certain open source software packages have been described as useful in implementing certain aspects of the present disclosure, it is to be understood that the present invention, as claimed, is directed not to any single step which may be known in the art, but to an inventive combination of steps producing a novel and useful result.

Although illustrative embodiments have been described with respect to individuals who have been diagnosed with psychosis, it will be appreciated that this is merely by way of illustrative example. The present disclosure is not limited to psychosis, and may be applied in respect of any psychiatric disorder for which auditory hallucinations are a symptom.

As can be seen from the above description, the technology described herein represents significantly more than merely using categories to organize, store and transmit information and organizing information through mathematical correlations. The technology is in fact an improvement to the technology of treatment support for diagnosed psychiatric conditions. The technology described herein provides a tool for objective external assessment of a user's progress in improving their ability to discriminate between an actual auditory sensory experience or is an occurrence of an acute auditory hallucinatory episode, and for notification of relevant third parties. This facilitates the ability of relevant personnel to provide treatment and support. As such, the technology is confined to psychiatric monitoring applications. Moreover, it is to be appreciated that the present technology is not directed to methods of medical treatment or even to methods of diagnosing a particular disorder; it is applied, inter alia, where a diagnosis has already been made by a human medical practitioner. The technology provides an objective technique for monitoring an individual's treatment progress within the context of an existing diagnosis, eliminating subjectivity by either doctor or patient. In this sense, the present technology provides a manually activated mechanical diagnostic tool to replace subjective perception with objective measurement. In this sense, the present technology, while innovative in its application and implementation, is analogous in its result to a manually initiated blood tests for (e.g.) triglyceride and cholesterol levels for individuals already diagnosed with cardiovascular disease. Just as the blood tests replaces a subjective assessment of "I have been getting better at following my diet" with an objective measure of actual progress that can be relied upon by user and practitioner, the present technology replaces an inherently subjective and unreliable assessment of the ability to distinguish between perceived and actual sounds with a reliable objective assessment.

The present technology may be embodied within a system, a method, a computer program product or any combination thereof. The computer program product may include a computer readable storage medium or media having computer readable program instructions thereon for causing a processor to carry out aspects of the present technology. The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing.

A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present technology may be assembler instructions, instruction-set-architecture (ISA) instructions, machine instructions, machine dependent instructions, microcode, firmware instructions, state-setting data, or either source code or object code written in any combination of one or more programming languages, including an object oriented programming language or a conventional procedural programming language. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to implement aspects of the present technology.

Aspects of the present technology have been described above with reference to flowchart illustrations and/or block diagrams of methods, apparatus (systems) and computer program products according to various embodiments. In this regard, the flowchart and block diagrams in the Figures illustrate the architecture, functionality, and operation of possible implementations of systems, methods and computer program products according to various embodiments of the present technology. For instance, each block in the flowchart or block diagrams may represent a module, segment, or portion of instructions, which comprises one or more executable instructions for implementing the specified logical function(s). It should also be noted that, in some alternative implementations, the functions noted in the block may occur out of the order noted in the Figures. For example, two blocks shown in succession may, in fact, be executed substantially concurrently, or the blocks may sometimes be executed in the reverse order, depending upon the functionality involved. Some specific examples of the foregoing may have been noted above but any such noted examples are not necessarily the only such examples. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

It also will be understood that each block of the flowchart illustrations and/or block diagrams, and combinations of blocks in the flowchart illustrations and/or block diagrams, can be implemented by computer program instructions. These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer readable program instructions may also be stored in a computer readable storage medium that can direct a computer, other programmable data processing apparatus, or other devices to function in a particular manner, such that the instructions stored in the computer readable storage medium produce an article of manufacture including instructions which implement aspects of the functions/acts specified in the flowchart and/or block diagram block or blocks. The computer readable program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

Figure 6:
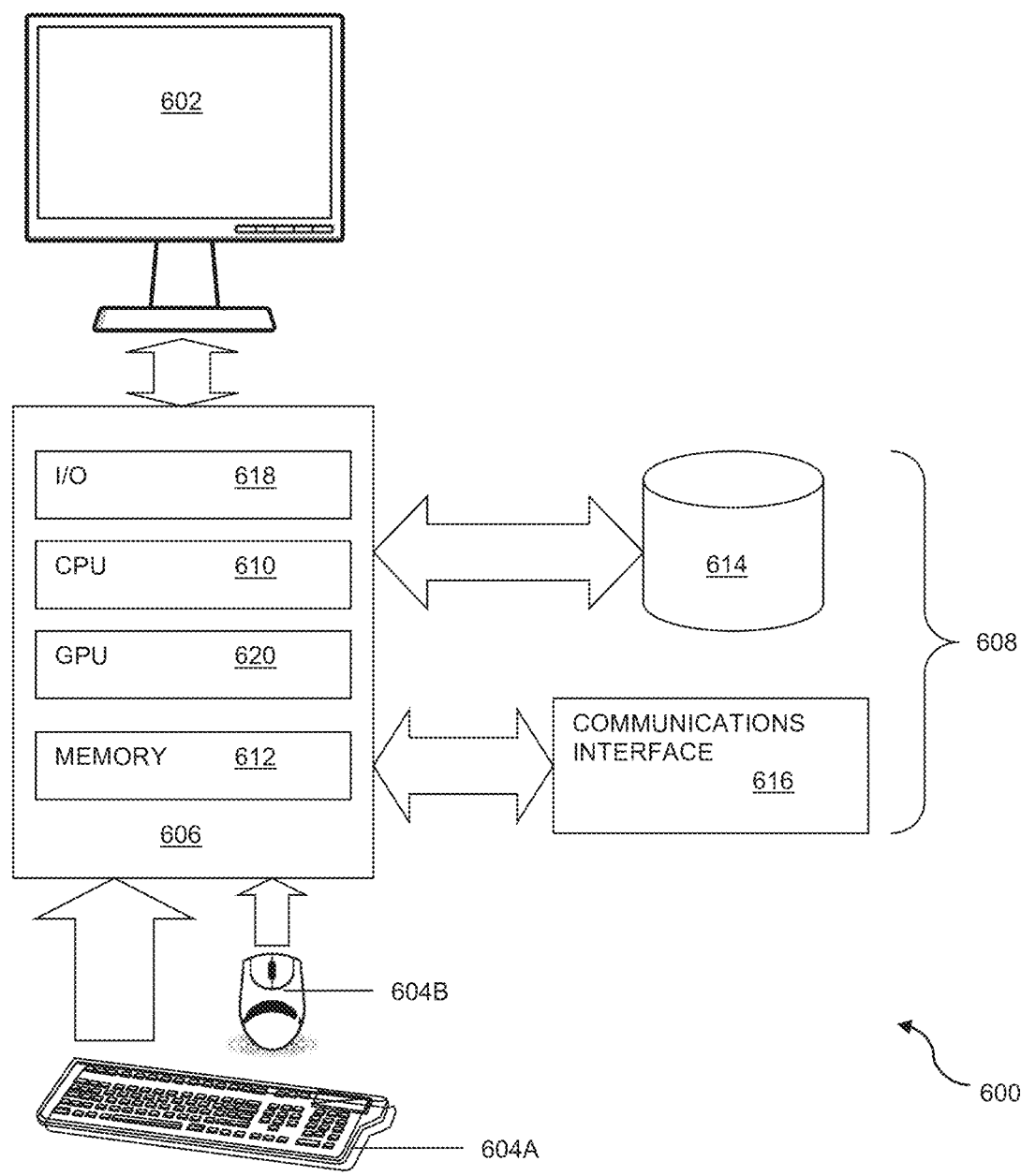
FIG. 6 shows an illustrative computer system in respect of which aspects of the present disclosure may be implemented.

An illustrative computer system in respect of which aspects of the technology herein described may be implemented is presented as a block diagram in FIG. 6. For example, the illustrative computer system 600 may be used to implement the remote computer system 112, as part of a dispatch system 126 associated with an ambulance or paramedic service 128, and/or part of a dedicated monitoring center 130, all as shown in FIG. 1.

The illustrative computer system is denoted generally by reference numeral 600 and includes a display 602, input devices in the form of keyboard 604A and pointing device 604B, computer 606 and external devices 608. While pointing device 604B is depicted as a mouse, it will be appreciated that other types of pointing device, or a touch screen, may also be used.

The computer 606 may contain one or more processors or microprocessors, such as a central processing unit (CPU) 610. The CPU 610 performs arithmetic calculations and control functions to execute software stored in an internal memory 612, preferably random access memory (RAM) and/or read only memory (ROM), and possibly additional memory 614. The additional memory 614 may include, for example, mass memory storage, hard disk drives, optical disk drives (including CD and DVD drives), magnetic disk drives, magnetic tape drives (including LTO, DLT, DAT and DCC), flash drives, program cartridges and cartridge interfaces such as those found in video game devices, removable memory chips such as EPROM or PROM, emerging storage media, such as holographic storage, or similar storage media as known in the art. This additional memory 614 may be physically internal to the computer 606, or external as shown in FIG. 6, or both.

The computer system 600 may also include other similar means for allowing computer programs or other instructions to be loaded. Such means can include, for example, a communications interface 616 which allows software and data to be transferred between the computer system 600 and external systems and networks. Examples of communications interface 616 can include a modem, a network interface such as an Ethernet card, a wireless communication interface, or a serial or parallel communications port. Software and data transferred via communications interface 616 are in the form of signals which can be electronic, acoustic, electromagnetic, optical or other signals capable of being received by communications interface 616. Multiple interfaces, of course, can be provided on a single computer system 600.

Input and output to and from the computer 606 is administered by the input/output (I/O) interface 618. This I/O interface 618 administers control of the display 602, keyboard 604A, external devices 608 and other such components of the computer system 600. The computer 606 also includes a graphical processing unit (GPU) 620. The latter may also be used for computational purposes as an adjunct to, or instead of, the (CPU) 610, for mathematical calculations.

The various components of the computer system 600 are coupled to one another either directly or by coupling to suitable buses.

Figure 7:
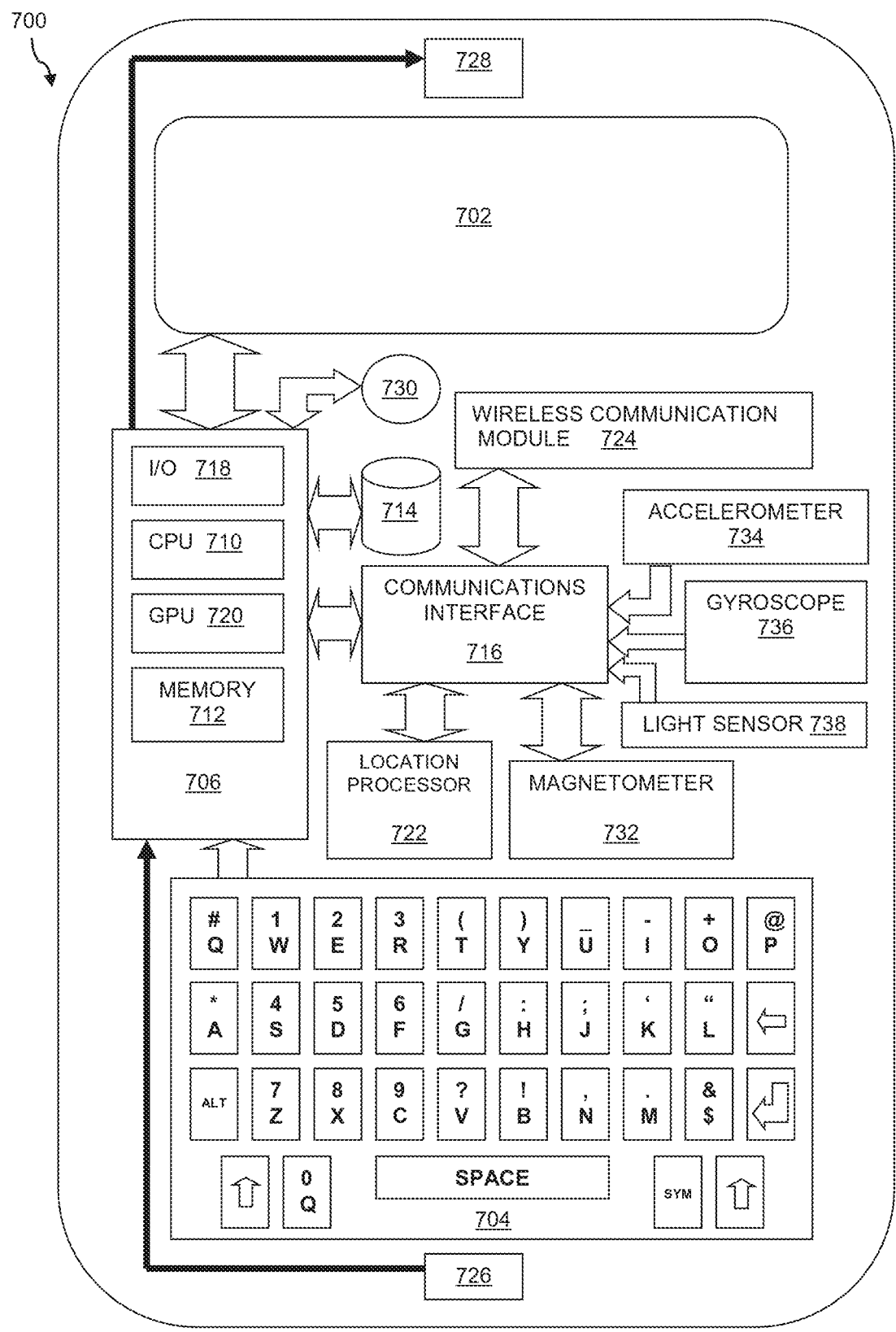
FIG. 7 shows an illustrative networked mobile wireless telecommunication computing device in respect of which aspects of the present disclosure may be implemented.

FIG. 7 shows an illustrative networked mobile wireless telecommunication computing device in the form of a smartphone 700. Thus, the smartphone 700 is an illustrative representation of the networked mobile wireless telecommunication computing device shown as a smartphone 104 in FIG. 1.

The smartphone 700 includes a display 702, an input device in the form of keyboard 704 and an onboard computer system 706. The display 702 may be a touchscreen display and thereby serve as an additional input device, or as an alternative to the keyboard 704. The onboard computer system 706 comprises a central processing unit (CPU) 710 having one or more processors or microprocessors for performing arithmetic calculations and control functions to execute software stored in an internal memory 712, preferably random access memory (RAM) and/or read only memory (ROM) is coupled to additional memory 714 which will typically comprise flash memory, which may be integrated into the smartphone 700 or may comprise a removable flash card, or both. The smartphone 700 also includes a communications interface 716 which allows software and data to be transferred between the smartphone 700 and external systems and networks. The communications interface 716 is coupled to one or more wireless communication modules 724, which will typically comprise a wireless radio for connecting to one or more of a cellular network, a wireless digital network or a Wi-Fi network. The communications interface 716 will also typically enable a wired connection of the smartphone 700 to an external computer system. A microphone 726 and speaker 728 are coupled to the onboard computer system 706 to support the telephone functions managed by the onboard computer system 706. Of note, the microphone 726 may be used to detect ambient sounds (e.g. ambient sounds 110 as shown in FIG. 1). A location services module 722 (e.g. including GPS receiver hardware) may also be coupled to the communications interface 716 to support navigation operations by the onboard computer system 706. One or more cameras 730 (e.g. front-facing and/or rear facing cameras) may also be coupled to the onboard computer system 706. A magnetometer 732 may also be coupled to the communications interface 716 to support navigation operations by the onboard computer system 706; the magnetometer functions as an electronic compass and gathers data used to determine the direction of magnetic North. An accelerometer 734 and gyroscope 736 are coupled to the communications interface 716 to gather data about movement of the smartphone 700. A light sensor 738 is also coupled to the communications interface 716. Input and output to and from the onboard computer system 706 is administered by the input/output (I/O) interface 718, which administers control of the display 702, keyboard 704, microphone 726, speaker 728 and camera(s) 730. The onboard computer system 706 may also include a separate graphical processing unit (GPU) 720. The various components are coupled to one another either directly or by coupling to suitable buses.

Without limitation, any one or more of the display 702 (if a touchscreen), keyboard 704, microphone 726, camera 730, accelerometer 734 and gyroscope 736 and light sensor 738 may be considered an input device that can be used to monitor for a deliberate overt activation action by the user.

The term "computer system", "computing device", "data processing system" and related terms, as used herein, are not limited to any particular type of computer system and encompasses servers, desktop computers, laptop computers, networked mobile wireless telecommunication computing devices such as smartphones, tablet computers, as well as other types of computer systems.

Thus, computer readable program code for implementing aspects of the technology described herein may be contained or stored in the memory 712 of the onboard computer system 706 of the smartphone 700 or the memory 612 of the computer 606, or on a computer usable or computer readable medium external to the onboard computer system 706 of the smartphone 700 or the computer 606, or on any combination thereof.

Finally, the terminology used herein is for the purpose of describing particular embodiments only and is not intended to be limiting. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description has been presented for purposes of illustration and description, but is not intended to be exhaustive or limited to the form disclosed. Many modifications and variations will be apparent to those of ordinary skill in the art without departing from the scope of the claims. The embodiment was chosen and described in order to best explain the principles of the technology and the practical application, and to enable others of ordinary skill in the art to understand the technology for various embodiments with various modifications as are suited to the particular use contemplated.

Certain illustrative embodiments have been described by way of example. It will be apparent to persons skilled in the art that a number of variations and modifications can be made without departing from the scope of the invention as defined in the claims. In construing the claims, it is to be understood that the use of a computing device to implement the embodiments described herein is essential.

What is claimed is:

1. A patient device for aiding psychosis patients with auditory psychosis symptoms, the patient device comprising:
   a microphone;
   a memory;
   a non-audio input device; and
      a processor configured to:
      monitor for a non-audio input to the non-audio input device of the patient device by a patient, wherein the non-audio input is a deliberate, overt activation action by the patient that represents an affirmative, unambiguous indication that the patient is hearing sounds potentially symptomatic of psychosis, wherein the deliberate, overt activation action by the patient that represents an affirmative, unambiguous indication that the patient is hearing sounds potentially symptomatic of psychosis launches a listening application;
      after launching the listening application:
      monitor external ambient sounds, as obtained by the microphone, and store information associated with the external ambient sounds in the memory;
      test the external ambient sounds against a threshold based on the information associated with the external ambient sounds in the memory; and
      responsive to both (i) the deliberate, overt activation action by the patient that represents the affirmative, unambiguous indication that the patient is hearing sounds potentially symptomatic of psychosis and (ii) determining that the external ambient sounds fail to satisfy the threshold based on the information associated with the external ambient sounds in the memory, transmit an alert indicating that the patient may be experiencing auditory psychosis symptoms.

2. The patient device of claim 1, wherein testing the external ambient sounds against the threshold comprises at least one of:
   testing the external ambient sounds against the threshold locally on the patient device; and
   testing the external ambient sounds against the threshold remotely by transmitting the information associated with the external ambient sounds from the patient device to a remote computer system and receiving threshold testing results from the remote computer system at the patient device.

3. The patient device of claim 1, wherein the non-audio input indicates a perception by the patient that they are hearing actual sounds.

4. The patient device of claim 3, wherein the processor is further configured to generate a report indicating correctness of a prior series of perception indications.

5. The patient device of claim 4, wherein the report comprises at least one of:
   recommendations for improving discrimination between auditory psychosis symptoms and external ambient sounds; and
   accuracy trends for perception indications to monitor progress of the patient over time.

6. The patient device of claim 1, wherein the external ambient sounds tested against the threshold include external ambient sounds immediately prior to the non-audio input and external ambient sounds following the non-audio input.

7. The patient device of claim 1, wherein the threshold is a minimum volume threshold.

8. The patient device of claim 1, wherein the threshold is a minimum confidence level associated with voice activity detection applied to the external ambient sounds.

9. A method aiding psychosis patients in distinguishing auditory psychosis symptoms, the method implemented on a patient device, the method comprising:
- monitoring, by the patient device, for a non-audio input into a non-audio input device of the patient device by a patient, wherein the non-audio input is a deliberate, overt activation action by the patient that represents an affirmative, unambiguous indication that the patient is hearing sounds potentially symptomatic of psychosis, wherein the deliberate, overt activation action by the patient that represents an affirmative, unambiguous indication that the patient is hearing sounds potentially symptomatic of psychosis launches a listening application;
- after launching the listening application:
  - monitoring external ambient sounds, as obtained by a microphone of the patient device, and storing information associated with the external ambient sounds in a memory of the patient device;
  - testing the external ambient sounds against a threshold based on the information associated with the external ambient sounds in the memory; and
  - responsive to both (i) the deliberate, overt activation action by the patient that represents the affirmative, unambiguous indication that the patient is hearing sounds potentially symptomatic of psychosis and (ii) determining that the external ambient sounds fail to satisfy the threshold based on the information associated with the external ambient sounds in the memory, transmitting an alert indicating that the patient may be experiencing auditory psychosis symptoms.

10. The method of claim 9, wherein testing the external ambient sounds against the threshold comprises at least one of:
- testing the external ambient sounds against the threshold locally on the patient device; and
- testing the external ambient sounds against the threshold remotely by transmitting the information associated with the external ambient sounds from the patient device to a remote computer system and receiving threshold testing results from the remote computer system at the patient device.

11. The method of claim 9, wherein the non-audio input indicates a perception by the patient that they are hearing actual sounds.

12. The method of claim 9, further comprising generating a report indicating correctness of a prior series of perception indications.

13. The method of claim 12, wherein the report comprises at least one of:
- recommendations for improving discrimination between auditory psychosis and external ambient sounds; and
- accuracy trends for perception indications to monitor progress of the patient over time.

14. The method of claim 9, wherein the external ambient sounds tested against the threshold include external ambient sounds immediately prior to the non-audio input and external ambient sounds following the non-audio input.

15. The method of claim 9, wherein the threshold is a minimum volume threshold.

16. The method of claim 9, wherein the threshold is a minimum confidence level associated with voice activity detection applied to the external ambient sounds.

17. One or more non-transitory computer-readable media comprising computer-executable instructions that, when executed by a patient device, causes the patient device to:
- monitor for a non-audio input to the non-audio input device of the patient device by a patient, wherein the non-audio input is a deliberate, overt activation action by the patient that represents an affirmative, unambiguous indication that the patient is hearing sounds potentially symptomatic of psychosis, wherein the deliberate, overt activation action by the patient that represents an affirmative, unambiguous indication that the patient is hearing sounds potentially symptomatic of psychosis launches a listening application;
- after launching the listening application:
  - monitor external ambient sounds, as obtained by a microphone of the patient device, and store information associated with the external ambient sounds in a memory of the patient device;
  - test the external ambient sounds against a threshold based on the information associated with the external ambient sounds in the memory; and
  - responsive to both (i) the deliberate, overt activation action by the patient that represents the affirmative, unambiguous indication that the patient is hearing sounds potentially symptomatic of psychosis and (ii) determining that the external ambient sounds fail to satisfy the threshold based on the information associated with the external ambient sounds in the memory, transmit an alert indicating that the patient may be experiencing auditory psychosis symptoms.

18. The one or more non-transitory computer-readable media of claim 17, wherein the instructions cause the patient device to do at least one of:
- test the external ambient sounds against the threshold locally on the patient device; and
- test the external ambient sounds against the threshold remotely by transmitting the information associated with the external ambient sounds from the patient device to a remote computer system and receiving threshold testing results from the remote computer system at the patient device.

19. The one or more non-transitory computer-readable media of claim 17,
wherein the non-audio input indicates a perception by the patient that they are hearing actual sounds.

20. The one or more non-transitory computer-readable media of claim 19,
wherein the instructions further cause the patient device to generate a report indicating correctness of a prior series of perception indications.

21. The one or more non-transitory computer-readable media of claim 20, wherein the report comprises at least one of:
- recommendations for improving discrimination between auditory psychosis symptoms and external ambient sounds; and
- accuracy trends for perception indications to monitor progress of the patient over time.

22. The one or more non-transitory computer-readable media of claim 17, wherein the external ambient sounds tested against the threshold include external ambient sounds immediately prior to the non-audio input and external ambient sounds following the non-audio input.

23. The one or more non-transitory computer-readable media of claim 17, wherein the non-audio input device is at least one of a touchscreen display, a keyboard, a camera, an accelerometer, a gyroscope, and a light sensor.

24. The one or more non-transitory computer-readable media of claim 17, wherein the threshold is a minimum volume threshold.

25. The one or more non-transitory computer-readable media of claim 17, wherein the threshold is a minimum confidence level associated with voice activity detection applied to the external ambient sounds.

* * * * *